United States Patent
Armstrong et al.

[11] Patent Number: 5,871,456
[45] Date of Patent: Feb. 16, 1999

[54] APPARATUS AND METHOD FOR CORRECTING FLAT, INVERTED OR RETRACTING NIPPLES OF VARYING SIZES

[76] Inventors: Edie C. Armstrong, 1011 Blue Coat Dr., Fairfax, Va. 22030; Judy A. Brady, 6161 Mississippi La., New Market, Md. 21774

[21] Appl. No.: 794,360

[22] Filed: Feb. 4, 1997

Related U.S. Application Data

[63] Continuation-in-part of Ser. No. 528,842, Sep. 15, 1995, abandoned.

[51] Int. Cl.⁶ .............................. A61H 7/00; A61M 1/00
[52] U.S. Cl. ............................................ 601/14; 604/316
[58] Field of Search .............................. 601/6, 7, 11, 14; 604/313–316; 606/201–204; 15/332, 416, 414

[56] References Cited

U.S. PATENT DOCUMENTS

| | | | |
|---|---|---|---|
| 655,747 | 8/1900 | Winckfield | 601/6 |
| 667,447 | 2/1901 | Miller | 601/14 |
| 1,212,845 | 1/1917 | Talley | 601/6 |
| 1,570,370 | 1/1926 | Brodersen et al. | 604/316 |
| 1,864,700 | 6/1932 | Wade | 604/314 |
| 2,068,496 | 1/1937 | Linghammar | 15/416 X |
| 2,295,817 | 9/1942 | Winther | 601/7 |
| 4,740,196 | 4/1988 | Powell | 601/14 X |
| 5,520,613 | 5/1996 | Copelan | 601/14 |
| 5,662,677 | 9/1997 | Wimmer | 604/313 X |

*Primary Examiner*—Danton D. DeMille
*Attorney, Agent, or Firm*—Skinner and Associates

[57] ABSTRACT

A device for correcting flat, inverted or retracting human nipples includes a tube having a piston inserted into one end and a removable, reversible tip attached to the other end. The tip is constructed from a flexible clear or semi-clear material. The tip is configurable by reversing its position to fit particular nipple sizes and/or to perform particular functions. Suction pressure is applied to evert the nipple by pulling the piston out of the tube. A method of using the device is also disclosed.

8 Claims, 4 Drawing Sheets

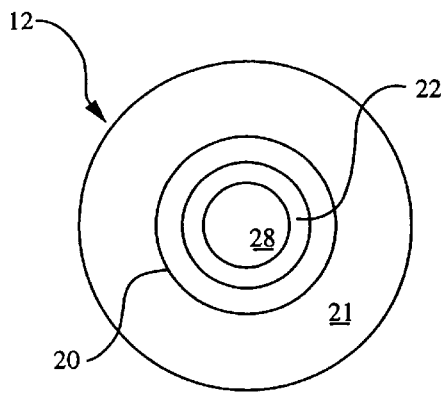
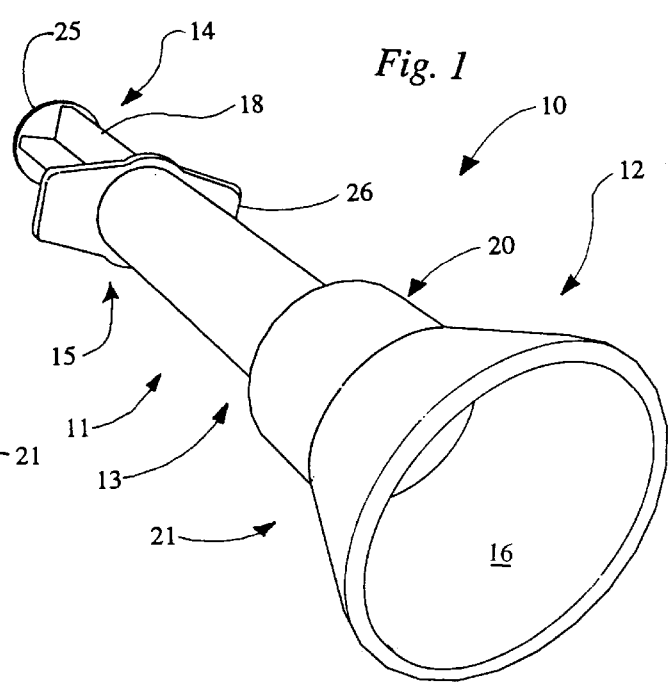
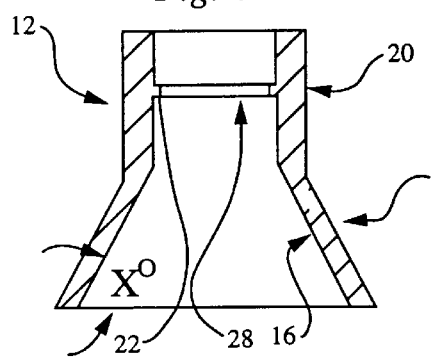
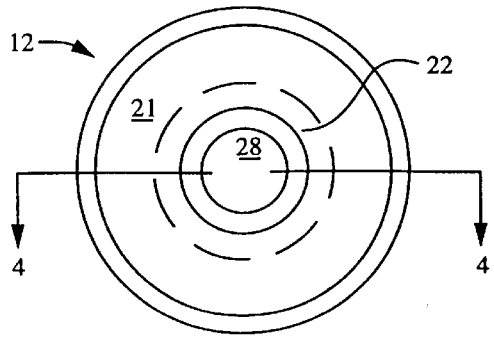

APPARATUS AND METHOD FOR CORRECTING FLAT, INVERTED OR RETRACTING NIPPLES OF VARYING SIZES

CROSS-REFERENCE TO RELATED APPLICATIONS

This application is a continuation in part of application Ser. No. 08/528,842, filed Sep. 15, 1995, now abandoned.

STATEMENT REGARDING FEDERALLY SPONSORED RESEARCH OR DEVELOPMENT

Not applicable.

REFERENCE TO A MICROFICHE APPENDIX

Not Applicable.

BACKGROUND OF THE INVENTION

1. Field of the Invention

The present invention relates, generally, to medical devices and methods, and, more particularly to a device for applying a gentle, controlled suction pressure to a human nipple/areola. The device and method are useful for correcting flat, inverted or retracting nipples to improve latch-on of an infant during breast feeding or for cosmetic reasons.

2. Background Information

A nipple flattens, retracts or inverts due to tiny bands of connective tissue, or adhesions, which attach the nipple to the breast tissue and pull the nipple inward. Flat, inverted or retracting nipples may be particularly troublesome to a woman who is attempting to breast feed her baby. If the baby is unable to latch onto the breast, the baby cannot feed and the lack of effective suckling could lead to lactation failure.

Various devices are known in the art for correction of flat, inverted or retracting nipples, i.e., devices which evert the nipple. One device used for treatment of inverted nipples is disclosed by Kesaree, et al., *Treatment of Inverted Nipples Using a Disposable Syringe,* J. Hum Lact 9(1), 1993, at 27–29. This device is constructed using a conventional syringe which is cut one centimeter from the nozzle. The piston is then inserted into the cut end and the smooth end is placed over the user's areola. The user then pulls out the piston to maintain a steady pressure and evert the nipple. A drawback of this device, however, is that it requires a cutting procedure to modify a syringe which is not designed to fit over a nipple. Further, if a user has a large nipple, the smooth end may not fit over the areola and the chances of damage to the nipple and surrounding tissue may be increased.

The NIPLETTE, which is manufactured by Cannon Babysafe, is also designed to correct inverted nipples. The Niplette includes a cap for placement over a nipple and a short tube connected to the cap. A syringe is connected to a valve at the open end of the tube to create suction pressure and evert the nipple. The syringe is then removed and the cap and tube are worn during the day and/or at night. A drawback of this device is that it must be worn continuously. In addition, the device may not be suitable for use on lactating breasts and is not recommended for use during the last two months of pregnancy. The device is also relatively expensive.

Another device for everting nipples is commonly known as a breast shell or milk cup. This device is worn prenatally and/or between feedings. A drawback of this device is that it sometimes promotes leakage of milk due to continuous pressure and is often not adequately ventilated, possibly causing skin breakdown. In addition, this device may cause mastitis due to pressure on tissue behind the nipple.

Another device which helps to evert the nipple is known as a nipple shield, which is worn over the nipple during breast feeding. Drawbacks of this device are that it decreases milk production with prolonged usage and may promote sore nipples and tissue breakdown by holding moisture next to the skin. Moreover, it is often necessary to use one hand to hold the device on the breast while breast feeding. Still another device for correcting flat, inverted or retracting nipples is a breast pump. This type of device often requires complicated assembly and may be quite costly.

Despite the need in the art for an apparatus and method of using the apparatus which overcome the disadvantages, shortcomings and limitations of the prior art, none insofar as is known has been developed.

BRIEF SUMMARY OF THE INVENTION

In accordance with a preferred embodiment of the invention, the device includes a tube having a tip removably attached thereto. Importantly, the tip is reversible to provide two different size and type nipple contact members. This permits quick and easy adjustment of the device to function on varying size and type nipples and to adjust the level and type of suction for varying needs.

It is an object of the present invention to provide a relatively low cost and safe device for correcting flat, inverted or retracting nipples.

It is another object of the invention to provide a device for correcting flat, inverted or retracting nipples which is easily assembled and simple to use.

It is another object of the invention to provide a device which permits viewing of the nipple during application and use.

It is another object of the invention to provide a device which is adjustable and permits use on varying sizes, shapes and types of nipples.

It is another object of the invention to provide a device for everting nipples which minimizes potential injury to the nipple/areolar tissue.

It is yet another object of the invention to provide a device which applies a gentle, controlled suction pressure to encourage the nipple to protrude, thereby enabling a baby to latch onto the nipple and breast feed effectively.

The features, benefits and objects of this invention will become clear to those skilled in the art by reference to the following description, claims and drawings.

BRIEF DESCRIPTION OF THE SEVERAL VIEWS OF THE DRAWING

FIG. 1 is a perspective view of the device of the present invention.

FIG. 3 is a sleeve end view of the tip of the device.

FIG. 4 is a crossectional view of the tip taken along line 4—4 of FIG. 3.

FIG. 5 is a conical end view of the tip.

DETAILED DESCRIPTION

Figure 2:
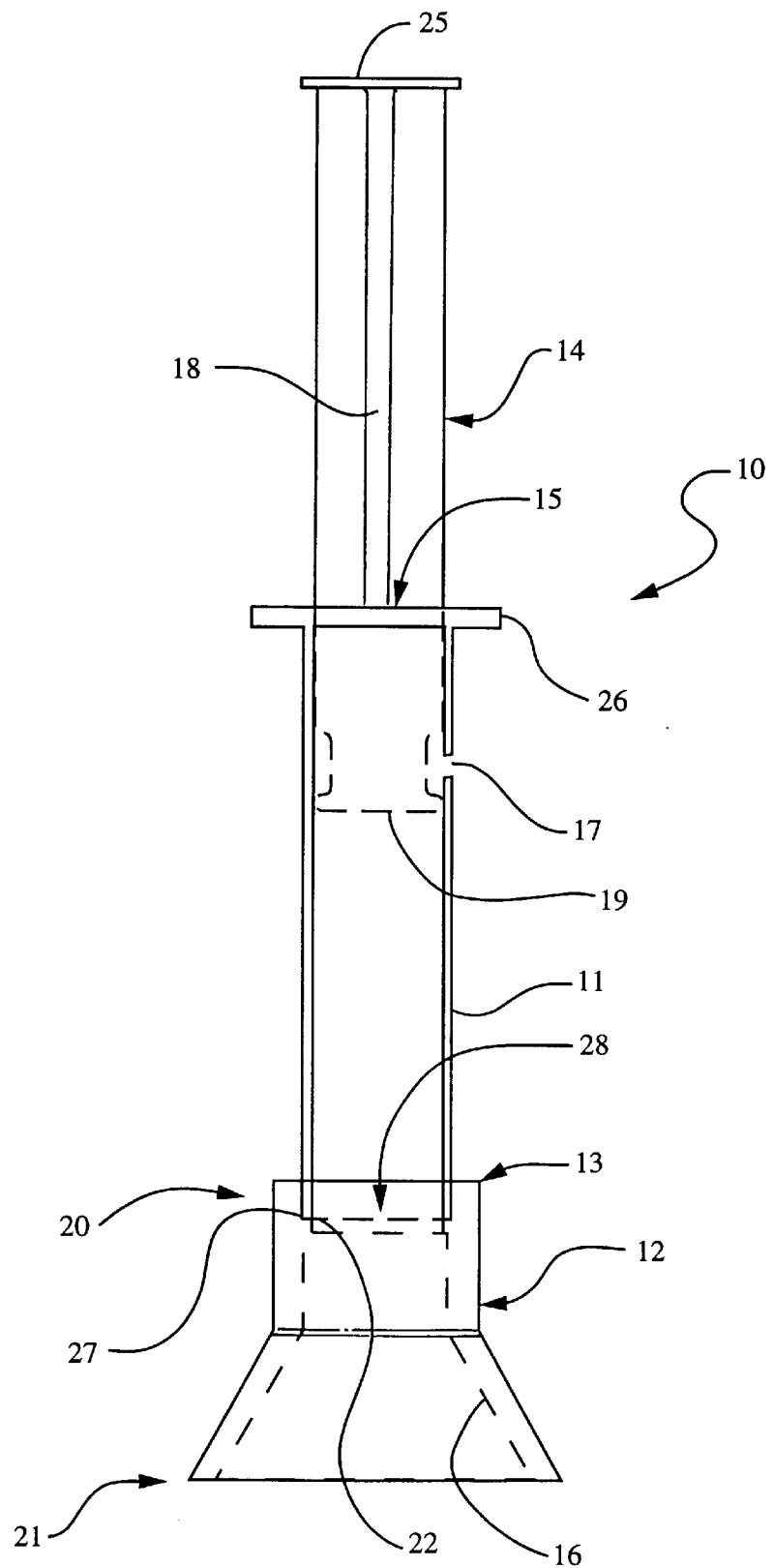
FIG. 2 is a side view of the device of the present invention showing internal components in phantom.
Figure 6A:
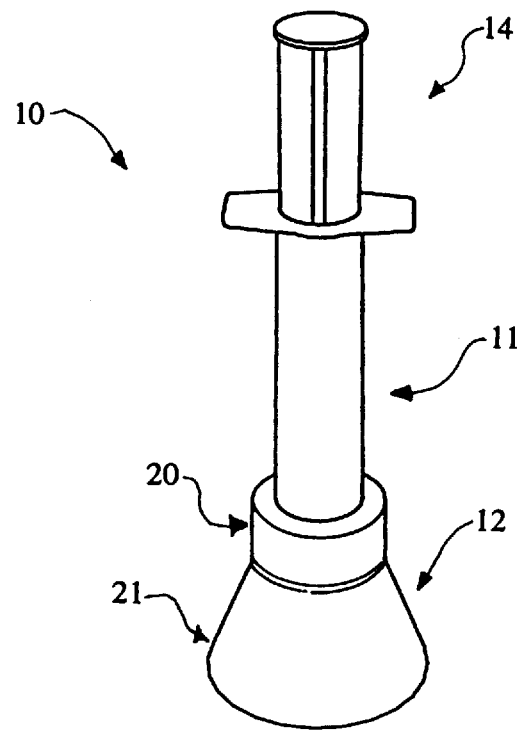
FIGS. 6a–d illustrate the reversible connection of the tip to the tube of the device.
Figure 6B:
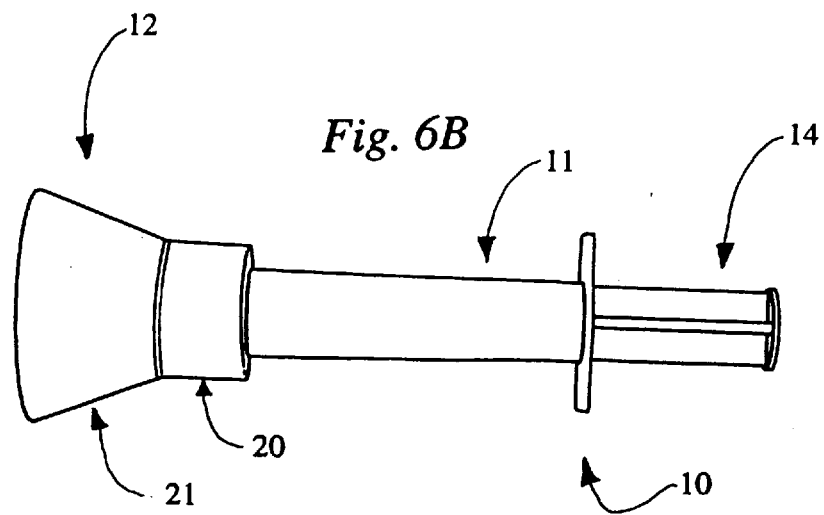
Figure 6C:
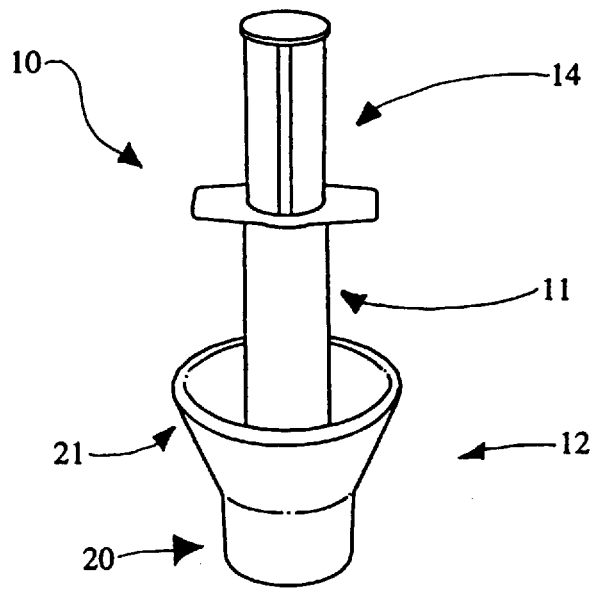
Figure 6D:
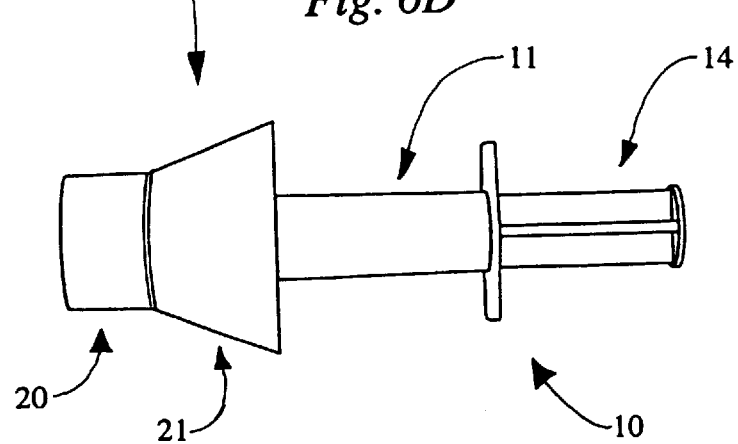

Device 10 basically comprises an elongated hollow tube 11 having a first or distal end 13 and a proximal or second end 15. A tip 12 is removably attached to a first end 13 of the tube 11. The tip 12 has a first end 20 and a second end 21. A piston 14 is inserted into a second end 15 of the tube 11.

The piston 14 preferably includes an elongated shaft member 18 and a seal creating end member 19 disposed at the distal end of the shaft 18. The piston 14 shaft 18 is constructed from a rigid plastic. It preferably has a handle or contact member 25 disposed at its proximal end for ease of grasping. The end member 19 is preferably constructed of an elastomeric material.

The tube 11 is preferably constructed of a rigid plastic material. It has a predetermined length, a predetermined inside diameter sufficient for insertion of the piston 14, and a predetermined outside diameter which permits it to be connected to the tip 12. Its second end 15 is open and preferably has a flange ring 26 for ease of grasping. Its first end 13 preferably has a radiused end portion 27 which is directed inwardly a small distance to create an end aperture 28 which has a diameter slightly smaller than its normal lengthwise inside diameter. This limits the piston from extending beyond the end of the tube during depression and hence prevents the piston from detaching the tip from the tube. It also prevents breast tissue from extending back into the hard tube barrel which causes skin trauma and discomfort.

At least the inner portion 16 (shown in phantom lines) of the tip 12, which comes in contact with the skin/nipple, is constructed from a soft, elastomeric latex, plastic or rubber material. Preferably, the entire tip 12 is constructed of a such material. The tip 12 material is preferably transparent or translucent to permit the user to view the nipple during initial placement and of the eversion of the nipple while the device is being used.

Importantly, the tip 12 is reversibly attachable to the first end 13 of the tube 11. That is to say that the tip 12 may be flipped over and attached from either of its ends 20 or 21 to the tube. The first end 20 has a cylindrical, sleeve-like configuration with a relatively small inside diameter which is substantially equivalent to the outside diameter of the tube 11. A sealing lip 22 is disposed a predetermined distance within the interior of the end 20. The sealing lip 22 creates a seal with the tube 11 when it is inserted in the first end 20. The lip further serves as a limit point for insertion of the tube 11 in the first end 20. The second end 21 has both a preferably cylindrical sleeve portion and a preferably conical expanded portion having an outer end with a larger diameter than that of the first end 20 or the sleeve portion. The expanded portion preferably has an interior portion 16 contoured to, upon the application of suction, receive and contact the skin of variously shaped breasts, specifically varying sizes and shapes of areolar tissue and nipples. The sleeve portion of the second end 21 has an inside diameter which is equivalent to that of the first end 20. The sealing lip 22 forms a divide between the first end 20 and the second end 21. The second end 21 of the tip and the sealing lip 22 create a seal with the tube 11 when it is inserted in the second end 21, the lip also serving as a limit point for insertion of the tube 11 in the second end 21. The tube is held connected to either end of the preferred embodiment of the tip by a friction fit between the outside diameter of the tube and the inside diameter of the cylindrical portion of the tip.

The reversible tip permits easy and fast fitting of the device 10 to the particular size of the breast, nipple and areola of the user. The need for the purchase and/or use of several different tip sizes may be obviated by this feature. This feature also permits adjustment of the feel of the device to the user, the fine positioning to a particular portion of the nipple/areola, and the suction power necessary for the particular nipple eversion exercise at hand. For example, by applying the wide, conical portion of the tip to the body suction is provided to both the nipple and the areolar tissue. This aids eversion of flat, retracting or inverted nipples to facilitate latch-on for breast feeding. It also may be used to help empty lactiferous sinuses behind the nipple and thereby enable the baby to latch-on and to help relieve engorgement. The conical end also accommodates larger nipples and a wide range of smaller nipple sizes. By applying the smaller sleeve end of the tip, a more direct, concentrated pressure is applied to the alone. This is used not only for everting flat, retracting or inverted nipples, but also enables stretching and breaking adhesions at the base of the nipples, encouraging the nipple to protrude optimally.

In summary, the reversible tip has advantages in terms of ease and convenience of use, speed of use and economy of use over a variety of nipple sizes and for a variety of particular procedures. The removablility of the tip 12 from the tube 11 also makes it easy to clean thoroughly. Finally, removable tip allows the substitution of tips which vary in size on a larger scale for use with a large variety of breast and nipple sizes and shapes.

The end 13 of the tube 11 preferably is friction fit into the tip 12. However, the tube 11 and tip 12 may alternatively include complementary screw threads. In yet another alternative, the tip 12 may be attached to end 13 by a snap connection or any other suitable attachment means.

In the embodiment shown, the expanded portion of the second end 21 of the tip 12 and the interior portion 16 is cone-shaped. However, the expanded portion and the interior portion 16 may be cylindrical, dome or bell-shaped. Similarly, although the tube 11 is generally a syringe having a cylindrical shape, other shapes, such as a rectangular-shaped tube may be used.

The maximum amount of suction available may be varied by increasing the size of the cylindrical tube 11. In general, however, suitable volumes for the cylindrical tube 11 range between 10 and 20 cubic centimeters. Suction may also be varied by using different tip sizes. Thus, for example, when the size of the tip 12 is increased and the size of the cylindrical tube 11 remains constant, it will be necessary to pull the piston 14 a greater distance out of the cylindrical tube 11 to achieve the same suction. Conversely, if the larger tube 11 is utilized and size of the tip 12 remains constant, then the distance that the piston 14 is pulled out of the cylindrical tube 11 must be reduced in order to achieve the same suction.

The tube 11 may include markings to indicate how far the piston 14 must be pulled out of the cylindrical tube 11 to achieve the same suction when a different size tip 12 is used. The tube 11 may also include other markings which are numbered, color-coded or the like, so that a user may easily identify the proper distance to pull out the piston 14 during subsequent use to achieve the desired result.

In another embodiment, the cylindrical tube 11 includes an aperture 17 in a side wall which provides a means for relieving pressure in the tube 11 when suction pressure reaches a predetermined level. The aperture 17 thus insures that excessive suction pressure will not be applied and thereby prevents damage to the nipple/areola.

In use, firstly, the piston 14 is inserted into the end 15 of the tube 11. Next, the tip is placed in proximity to the nipple and the two ends of the tip and compared with the nipple size to determine which end best fits the nipple. After this is determined, the opposite end of the tip 12 is attached to the other end 13 of the tube 11. Subsequently, the outwardly disposed tip 12 end is placed over the nipple of the user and pressed against the skin of the breast. Finally, the piston 14 pulled out of the tube 11 until the proper amount of pressure is applied. When proper pressure is applied, the nipple should evert into the tip 12. The tip 12 is then removed from the breast and the baby is presented to latch-on to the everted nipple. If the user experiences any pain, she can easily relieve the pressure by pushing the piston 14 back into the tube 11 or she can break suction by inserting a finger between the seal and the skin. After suction has been applied for the appropriate time period, piston 14 should be pushed completely into the tube 11 to release essentially all suction pressure and allow the device to be removed without causing trauma to the nipple and surrounding tissue. The device may be used several times a day, for example, just prior to the baby latching-on during breast feeding. A flat, inverted or retracting nipple is everted by the user simply applying a steady, gentle pressure using the device 10 for approximately 30 to 60 seconds, although additional time may be required.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A method for correcting a flat, inverted or retracting human breast nipple, comprising:
   (a) providing a device comprising:
      (i) a tube having first and second ends;
      (ii) a tip having a predetermined configuration with first and second ends, said second end comprising a sleeve portion connected to said first end and an expanded portion extending from said sleeve portion, said tip being reversible as both said first end and said sleeve portion of said second end are adapted for attachment to said first end of said tube and for effective and comfortable contact with a breast; said first and second ends comprising a flexible material capable of providing a seal around a nipple, said expanded portion having an interior portion for receiving and contacting varying sizes and shapes of breasts, areolar tissue and nipples, said first end and said sleeve portion of said second end form a tip cylindrical portion, said cylindrical portion having a predetermined inside diameter, a predetermined length and an annular sealing lip disposed interiorly at a predetermined portion along its length between said first end and said sleeve portion of said second end; and
      (iii) a piston insertable into said second end of said tube and retractable within said tube for creating suction pressure in said tube when said tip is placed over a nipple, said suction pressure being applied against said breast to correct flat, inverted or retracting nipples;
   (b) selecting an end of said tip for contact with the breast by matching the size of the end with the nipple;
   (c) attaching an end of said tip opposite said selected contact end to said first end of said tube;
   (d) inserting said piston a predetermined distance into said tube through said second end of said tube;
   (e) placing said contact end of said tip on the breast over the nipple; and
   (f) retracting said piston in said tube to apply said suction pressure to the nipple.

2. The method according to claim 1, wherein said device has the following features: said first end and said sleeve portion form a cylindrical portion and said expanded portion forms a conical portion connected to said cylindrical portion, said cylindrical portion having a predetermined inside diameter, a predetermined length and an annular sealing lip disposed between said first end and said sleeve portion of said second end, said conical portion having a maximum inside diameter which is greater than said cylindrical portion inside diameter, and said tube having a predetermined outside diameter which is substantially equivalent to said tip cylindrical portion inside diameter whereby said tube is connected to said tip by a friction fit between said tube inserted in said cylindrical portion and abutting against said sealing lip, said tip being reversible whereby said tube first end is insertable into said first or said second end of said tip and lodges in said tip cylindrical portion.

3. A device for correcting flat, inverted or retracting human breast nipples, comprising:
   a tube having first and second ends;
   a tip having a predetermined configuration with first and second ends, said second end comprising a sleeve portion connected to said first end and an expanded portion extending from said sleeve portion, said first end and said sleeve portion of said second end form a tip cylindrical portion, said cylindrical portion having a predetermined inside diameter, a predetermined length and an annular sealing lip disposed interiorly at a predetermined portion along its length between said first end and said sleeve portion of said second end, said tip being reversible as both said first end and said sleeve portion of said second end are adapted for attachment to said first end of said tube, said first end and said second end of said tip being adapted for effective and comfortable contact with a breast, said first and second ends comprising a flexible material capable of providing a seal around a nipple, said expanded portion having an interior portion for receiving and contacting varying sizes and shapes of breasts, areolar tissue and nipples; and
   a piston insertable into said second end of said tube and retractable within said tube for creating suction pressure in said tube when said tip is placed over a nipple, said suction pressure being applied against said breast to correct flat, inverted or retracting nipples.

4. The device according to claim 3 wherein said tip is constructed of a material selected from the group consisting of soft latex, plastic or rubber material.

5. The device according to claim 4, wherein said expanded portion forms a conical portion connected to said cylindrical portion, said conical portion having a maximum inside diameter which is greater than said cylindrical portion inside diameter, and said tube having a predetermined outside diameter which is substantially equivalent to said tip cylindrical portion inside diameter whereby said tube is connected to said tip by a friction fit between said tube inserted in said cylindrical portion and abutting against said sealing lip, said tip being reversible whereby said tube first end is insertable into said first or said second end of said tip and lodges in said tip cylindrical portion.

6. The device according to claim 3 wherein said expanded portion of said second end forms a conical portion connected to said cylindrical portion.

7. The device according to claim 6, wherein said cylindrical portion has a predetermined inside diameter and said tube has a predetermined outside diameter which is substantially equivalent to said tip cylindrical portion inside diameter, said tube being connected to said tip by a friction fit between said tube inserted in said cylindrical portion.

8. The device according to claim 7, wherein said conical portion has a maximum inside diameter which is greater than said cylindrical portion inside diameter.

* * * * *